US006995298B1

(12) United States Patent
Law et al.

(10) Patent No.: US 6,995,298 B1
(45) Date of Patent: Feb. 7, 2006

(54) TRANSGENIC MAMMALS EXPRESSING MUTANT GP IIIA

(75) Inventors: Deborah Ann Law, San Francisco, CA (US); David R. Phillips, San Mateo, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/673,302

(22) PCT Filed: Apr. 15, 1998

(86) PCT No.: PCT/US99/08285

§ 371 (c)(1),
(2), (4) Date: Mar. 23, 2001

(87) PCT Pub. No.: WO99/53032

PCT Pub. Date: Oct. 21, 1999

Related U.S. Application Data

(60) Provisional application No. 60/115,516, filed on Apr. 15, 1998.

(51) Int. Cl.
*G01N 33/00* (2006.01)
*A01K 67/027* (2006.01)
*C12N 15/00* (2006.01)
*C12N 15/63* (2006.01)
*A01N 63/00* (2006.01)

(52) U.S. Cl. ............................. 800/3; 800/18; 800/21; 800/22; 800/25; 435/320.1; 435/455; 424/93.21; 536/23.5

(58) Field of Classification Search ................ 435/455, 435/320.1, 463, 325; 800/18, 21, 22, 25, 800/3, 13, 14; 424/93.21; 536/23.5
See application file for complete search history.

(56) References Cited

FOREIGN PATENT DOCUMENTS

| WO | WO 95/25173 | 9/1995 |
| WO | WO 97/08316 | 3/1997 |

OTHER PUBLICATIONS

Wall; Transgenic Livestock: Progress and Prospective for the Future, 1996, Theriogenology 45: 57-68.*
Houdebine; Production of pharmaceutical proteins from transgenic animals, 1994, Journal of Biotechnology 34: 269-287.*
Hammer et. al.; Genetic Egineering of Mammalian Enbryos. 1996. J. Anim. Sci. 63: 269-278.*
Ebert et. al.; A Moloney MLV-Rat Somatitropin Fusion Gene Produces Biologically Active Somatotropin in a Transgenic Pig. 1988, Molecular Endocrinol 2: 277-283. ogy.*
Mullins et. al.; Perspectives Series: Molecular Medicine in Genetically Engineered Animals. 1996. J. Clin. Invest. vol. 97, No. 7 1557-1560.*
Kappel et. al.; Regulating gene expression in transgenic animals, 1992, Current Opinion in Biotechnology #: 548-553.*
Strojek et. al.; The Use of Transgenic Animal Technques for Livestock Improvement ; 1988, Genetic Engineering: Principles and methods vol. 10: 221-246.*
Moreadith et. al.; Gene targeting in embryonic stem cells: the new physiology and metabolism, 1997. J. Moi. Med. 75: 208-216.*
Kappel et al., 1992, Current Opinion in Biotechnology, vol. 3, p. 548-553.*
Sigmund, Jun. 2000, Arterioscler. Thromb. Vasc. Biol., p. 1425-1429.*
Houdebine, L-M., 2002, Journal of Biotechnology, vol. 98, p. 145-160.*
Baudoin et al. (Apr. 1998) Knockout and knockin of the β1 exon D define distinct roles for integrin splice variants in heart function and embryonic development, Genes Dev. 12:1202-1216. (Cold Spring Harbor Press, NY, USA).
Blystone et al. (Nov. 1997) Requirement of integrin $\beta_3$ tyrosine 747 for $\beta_3$ tyrosine phosphorylation and regulation of $\alpha_v\beta_3$ avidity, J. Biol. Chem. 272:28757-28761 (American Society for Biochemistry and Molecular Biology, Bethesda, MD, USA).
Hanks et al. (1995) Rescue of the En-1 mutant phenotype by replacement of En-1 with En-2, Science 269: 679-682 (American Association for the Advancement of Science, Washington, DC, USA).
Liu et al. (1996) Identification of a functionally important sequence in the cytoplasmic tail of integrin $\beta_3$ by using cell-permeable peptide analogs, Proc. Natl. Acad. Sci. USA 93:11819-11824 (Nat'l. Acad. Sciences, Washington, DC, USA).
International Search Report PCT/US99/08285, mailed Aug. 30, 1999.

* cited by examiner

Primary Examiner—Shin-Lin Chen
(74) Attorney, Agent, or Firm—Millennium Pharmaceuticals Inc.

(57) ABSTRACT

The present invention relates to mammals into which foreign DNA has been introduced or in which various modifications or substitutions have been made to an integrin β subunit, thereby generating transgenic or genetically-engineered non-human mammals. In particular, the present invention provides a transgenic mammal in which the endogenous GP IIIa gene has been replaced with an altered or mutant GP IIIa gene in which one or all of the phosphorylable cytoplasmic tyrosine residues have been replaced with non-tyrosine residues such as phenylalanine. Since the platelets in the blood of the resultant transgenic mammals expressing in wild-type mammals, these genetically-engineered animals provide a critical tool for assessing the importance of the phosphorylation reaction for platelet function. The invention is also useful for studying the effect of the mutant GP IIIa integrin subunit on biological processes other than platelet formation.

18 Claims, 2 Drawing Sheets

FIG. 1

| | | | | |
|---|---|---|---|---|
| GP IIIa (β3) | KlLLtTHDRk | EFAKFEeEra | rAkWdtanNP | LYKeAt©Tft | ..........Ni | tYrgt...... ........ |
| β6 | KLLVsfHDRk | EvAKFEaErs | kAkWqtgtNP | LYrgstsTfk | ..........Nv | tYkhrekqkv dlstdc |
| β1 | KLLmlIHDRR | EEAKEEKkm.. | nAkWdtgeNP | iYKsAvtIvv | ..........Np | kYegk...... ........ |
| β5 | KLLVtIHDRR | EFAKFqsErs | rArYemasNP | LYrkpisTht | vdftfnkfNk | sYngtvd... ........ |
| β2 | KalThisDIR | EYrrFEkEkl | ksqWnnd.NP | LFKsAtTIvm | ..........Np | kFaes...... ........ |
| β7 | rLsVelyDRR | EYsrFEkEqq | qlnWkqdsNP | LYKsAltTti | ..........Np | rFqeadsptl ........ |
| Cn | KLLV-IHDRR | EFAKFE-E-- | -A-W----NP | LYK-A--T-- | ----------N- | -Y------ -------- |

FIG. 2

TRANSGENIC MAMMALS EXPRESSING MUTANT GP IIIA

CROSS REFERENCE TO RELATED APPLICATIONS

This application is a National Stage Application of PCT International Application No. PCT/US99/08285, filed Apr. 15, 1999, and claims priority under 35 U.S.C. § 119(e) to U.S. Provisional Patent Application No. 60/115,516, filed Apr. 15, 1998, now abandoned, incorporated by reference herein in its entirety.

FIELD OF THE INVENTION

The present invention relates to mammals into which foreign DNA has been introduced or in which certain codons of integrin-encoding genes have been replaced, thereby generating transgenic or genetically-engineered mammals. In particular, the present invention provides a transgenic mammal in which the endogenous GP IIIa gene (also known as β3) has been replaced in whole or in part with a mutant GP IIIa gene in which one or both of the two phosphorylatable cytoplasmic tyrosine residues have been replaced with non-tyrosine residues, for example, such as phenylalanine. Since the cells, platelets in particular, that are found in the blood of the resultant transgenic mammals that express an altered GP IIIa gene cannot undergo tyrosine phosphorylation, either in whole or in part, as occurs in their wild type counterparts, these animals provide a useful tool for assessing the importance of the phosphorylation of these tyrosine residues for platelet function. The present invention is also useful for studying the effect of the mutant GP IIIa integrin subunit on biological processes other than platelet formation.

BACKGROUND OF THE INVENTION

This application is related to U.S. patent application Ser. No. 08/734,607, filed Oct. 18, 1996, now U.S. Pat. No. 6,210,913; U.S. Provisional Application No. 60/031,665, filed Nov. 21, 1996; U.S. Provisional Application No. 60/042,093, filed Mar. 28, 1997; and, U.S. patent application Ser. No. 08/975,653, filed Nov. 21, 1997. All of the publications and patent applications that are identified in this specification are hereby incorporated by reference to the same extent as if each individual publication or patent application was specifically and individually indicated to be incorporated by reference.

A. Integrins

Integrins are a family of αβ heterodimers that mediate adhesion of cells to extracellular matrix proteins and to other cells (Clark et al., Science (1995) 268:233–239). Integrins also bind to the actin cytoskeleton through a series of intermediate proteins, and thus provide a link between the extracellular matrix and the intracellular cytoskeleton and its associated motile machinery. Such transmembrane linkages are required for cell migration. Many biological responses are dependent at least to some extent upon integrin-mediated adhesion and cell migration, including embryonic development, hemostasis, clot retraction, mitosis, angiogenesis, inflammation, immune response, leukocyte horning and activation, phagocytosis, bone resorption, tumor growth and metastasis, atherosclerosis, restenosis and wound healing.

Members of the integrin family also participate in signal transduction. This is evidenced by an alteration in the adhesive affinity of cell surface integrins in response to cellular activation, termed inside-out signal transduction. Additionally, effects on intracellular signaling pathways following integrin-mediated adhesion have been observed, termed outside-in signal transduction.

Figure 1:
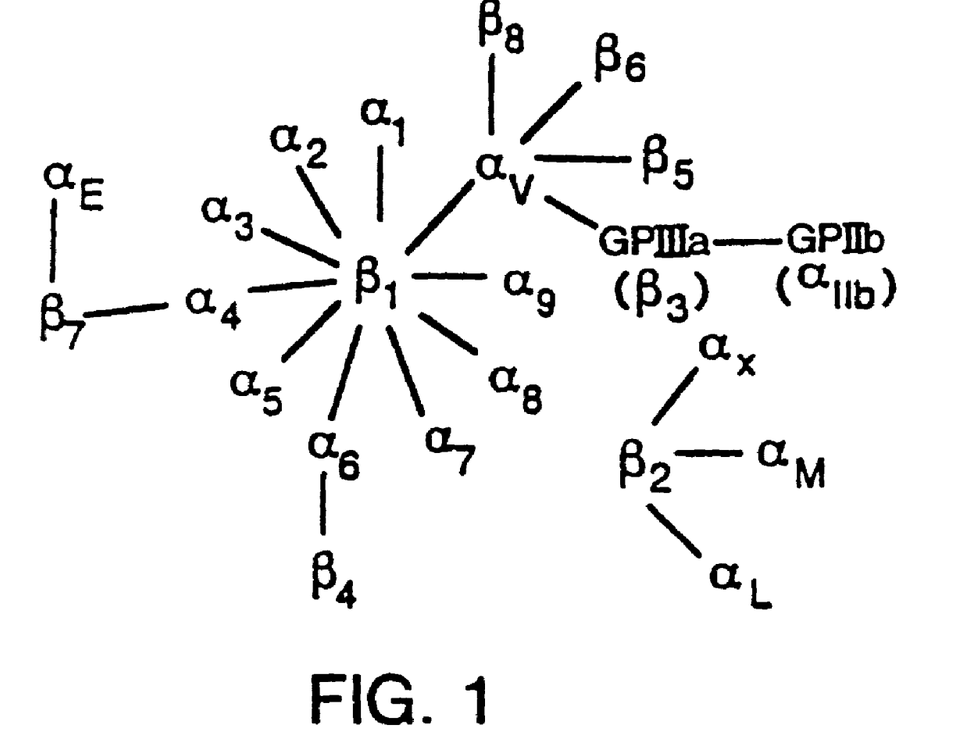
FIG. 1 shows the pairing of α and β integrin subunits.

The integrin family consists of 15 related known α subunits (α1, α2, α3, α4, α5, α6, α7, α8, α9, αE, αV, αIIb, αL, αM, and αX) and 8 related known β subunits (β1, β2, β3, β4, β5, β6, β7, and β8). Luscinskas et al., *FASEB J.*, 8: 929–938 (1994). Integrin α and β subunits are known to exist in a variety of pairings as indicated in FIG. 1. Integrin ligand specificity is determined by the specific pairing of the α and β subunits, although some redundancy exists as several of the integrins are known to bind the same ligand.

Two known parings of the β3 subunit have been observed: with αV to make αVβ3, the Vitronectin Receptor; and with GP IIb to make GP IIb–IIIa, the Fibrinogen Receptor. αVβ3 is widely distributed, is the most promiscuous member of the integrin family and mediates cellular attachment to a wide spectrum of adhesive proteins, mostly at the R-G-D sequence on the adhesive protein. The biological processes mediated by αVβ3 are diverse and include bone resorption, angiogenesis, tumor metastasis and restenosis. αVβ3 is known to signal upon adhesive protein ligation (P. I. Leavesley, et al., *J. Cell Biol.* 121:163–170 (1993)). As an example, endothelial cells undergo apoptosis when relieved of ligation (P. C. Brooks, *Cell* 79:1157–1164 (1994)).

B. Interaction of Integrins with Known Cytoskeletal Proteins

The binding of unmodified α and β subunit cytoplasmic domains of integrins to a variety of cytoskeletal and signaling proteins has been documented. S. Dedhar et al., *Curr. Opin. Cell Biol.* 8:657–669 (1996). Morphological studies have shown that many of these proteins are concentrated in focal adhesions where integrins cluster and bind to both the extracellular matrix and cytoskeletal proteins. I. Knezevic et al., *J. Biol. Chem.* 271(27):16416–16521 (1996).

For example, talin, a 235 kD vinculin and actin binding protein, binds to the cytoplasmic domains of αIIb and β3 in a solid phase binding assay. I. Knezevic et al., Id. The binding of α actinin, a 100 kD vinculin binding protein and actin cross-linking protein, to the cytoplasmic domain of β1 and β3 in solid phase binding assays has also been observed. C. A. Otey et al., *J. Biol. Chem.* 268(28); 21193–21197 (1993); and C. A. Otey et al., *J. Cell Biol.* 111:721–729 (1990). Binding studies have demonstrated an interaction between the cytoplasmic domain of β1 and tensin, a 215 kD SH2 domain containing vinculin and actin binding protein. S. Lin et al. *Mol. Biol. Cell* 7 Supp. 389a, Abstract 2259 (1996).

Other cytoskeletal related proteins also interact with integrins. Skelemin, a 195 kD myosin and intermediate filament binding protein, binds to the membrane proximal regions of β1 and β3 cytoplasmic domains. K. B. Reddy et al., *Mol. Biol. Cell* 7 Supp. 385A, Abstract 2237 (1995). These authors suggested that skelemin could link myosin and intermediate filaments to β integrins.

Paxillin, a vinculin binding signaling protein also binds to the cytoplasmic domain of the β1 integrin. M. D. Schaller et al., *J. Cell Biol.* 130:1181–1187 (1995). It is not yet known whether the β1-paxillin association is direct or indirect, however paxillin was postulated as being the substrate for and tyrosine phosphorylated by tyrosine kinase pp125 FAK. The actin binding protein filamin has been shown to bind to the cytoplasmic tail of the β2 integrin subunit in vitro and co-immunoprecipitated and co-localized with β2 integrins in vivo. C. P. Sharma et al., *J. Immunol.* 154; 3461–3470 (1995).

A 208 kD integrin binding protein identified as being related to the myosin light chain kinase family of serine/threonine kinases has also been reported. Walker et al., *Mol. Biol. Cell* 7 Supp. 385A, Abstract 2235 (1995). This kinase was said to be part of a complex of proteins including α-actinin and myosin, however, it was unclear whether the kinase associated directly with the cytoplasmic tails of integrins or through a complex of proteins.

Although the cytoskeletal proteins listed above have been shown to interact with cytoplasmic domains of integrin subunits with purified proteins or peptides, it is not known how these interactions occur within cells or how these interactions are regulated. Furthermore, the integrin/cytoskeletal interactions described thus far do not occur in a phosphotyrosine-dependent manner.

C. Tyrosine Phosphorylation of the Cytoplasmic Domain of Integrin β Subunits

Platelet aggregation induced by a number of agonists results in the phosphorylation of tyrosine residues in the β3 cytoplasmic tail. Law et al., *J. Biol. Chem* 271:10811–10815 (1996). In some respects, the phosphorylation of both tyrosine residues was necessary for binding to certain signaling proteins, whereas other signaling proteins bound following monophosphorylation. Furthermore, adhesion to vitronectin by cells transfected with αvβ3 induces a robust tyrosine phosphorylation of the β3 subunit. Blystone et al., *J. Biol. Chem* 271:31458–31462 (1996).

Studies have shown that the sequences of the cytoplasmic domains of β1, β2 and β3 which contain tyrosines are important for normal integrin/cytoskeletal interactions. For example, the substitution of tyrosine 747 by alanine in β3 transfected into CHO cells abolished β3-mediated cell spreading, blocked the recruitment of αIIbβ3 to preestablished adhesion plaques, and decreased the ability of αIIbβ3 to mediate internalization of fibrinogen-coated particles. J. Ylanne et. al., *J. Biol. Chem.,* 270, 9550–9557, (1995).

Additional experiments reported by Ylanne et al., Id., showed further that substitution of alanine for tyrosine 759 decreased cell spreading and the recruitment of αIIbβ3 to adhesion plaques, while deletion of the carboxy terminal pentapeptide that contains this sequence had an even more pronounced effect on the function of the integrin. These authors concluded integrin-mediated cell spreading does not occur because the factors that are absolutely required for integrin-mediated cell spreading cannot bind either the β3 truncated at residue 757 or the integrin with tyrosine 747 of β3 substituted by alanine.

Point mutations in homologous domains in β1- and β2-containing integrins also modulate function, as these mutations affect integrin-cytoskeletal interactions by reducing focal adhesions, A. A. Reszka et. al., *J. Cell Biol.* 117:1321–1330 (1992), and integrin activation, M. L. Hibbs et. al., *J. Exp. Med.* 174:1227–1238 (1991), respectively. Tyrosine kinases similarly were found to be essential in regulating the cytoskeletal attachment of αIIbβ3. Schoenwaelder et al., *J. Biol. Chem.* 269(51):32479–32487 (1994).

Overall, the interactions between the two tyrosines and the "cell adhesion regulatory domain" or "CARD" of residues 747–762 of the β3 cytoplasmic domain were reported to be essential for regulation of the adhesive function of integrin β3. Liu et al., *PNAS* 93:11819–11824 (1996). A 16-amino acid sequence from the CARD inhibited adhesion of HEL and ECV 304 cells to immobilized fibrinogen by competing with intracellular protein-protein interactions that "engage the business end" of the integrin β3 tail. However, the identity of cytoplasmic protein(s) interacting with CARD was said to remain to be established.

D. Myosin

The platelet plasma membrane is coated by a lattice-like structure, known as the membrane skeleton, that is composed of short actin filaments, actin-binding protein, spectrin, vinculin and various other proteins, not all yet identified. Fox et al., *J. Biol. Chem.* 268(34):25973–25984 (1993). On the cytoplasmic side, the skeleton appears to be associated with a network of cytoplasmic actin filaments. The membrane skeleton coats the lipid bilayer and is associated with both extracellular glycoproteins and intracellular cytoskeletal elements. Fox et al. suggested that GPIIb–IIIa induces redistribution of components of the membrane skeleton and associated signaling molecules as a step in regulating integrin-induced motile events in platelets.

Myosin is a contractile protein that interacts with actin to produce contraction or movement. The term "myosin" broadly refers to a diverse superfamily, comprised of at least 11 classes, of molecular motors capable of translocating actin filaments or of translocating vesicles or other cargo on fixed actin filaments by. One characteristic of all myosins is their ability to reversibly bind to actin and to hydrolyze MgATP. See FIG. 5 and J. R. Sellers and H. V. Goodson, Protein Profile 2:1323–1339 (1995).

All types of myosin that have been purified are multimeric and appear to possess at least three functional domains—a head, neck and tail. The head or motor domain contains nucleotide and actin binding sites and is the most conserved region of the myosin superfamily. The neck domain consists of a long single alpha helical strand from the heavy chain which is stabilized by the binding of light chain subunits. The tail region, which serves to anchor myosin so that it can translocate actin, is the most diverse primary sequence of all the regions and may serve to anchor certain myosin isoforms to cell or organelle membranes. It has been suggested that myosin clustering within a cell may occur on membranes or on actin filaments themselves. Titus, *Trends in Cell Biology* 7:119 (1997). However, the precise biochemical mechanism of interaction between the myosin tail and cytocellular structures has not heretofore been described.

E. Signal Transduction

The involvement of the cytoplasmic domain of GP IIb–IIIa in integrin signal transduction is inferred from mutagenesis experiments. Deletion of the cytoplasmic domain of GP IIb results in a constitutively active receptor that binds fibrinogen with an affinity equivalent to the wild-type complex, implying that the cytoplasmic tail of GP IIb has a regulatory role (T. E. O'Toole, et al., *Cell Regul.* 1:883–893, (1990)). Point mutations, deletions and other truncations of GP IIb–IIIa affects the ligand binding activity of GP IIb–IIIa and its signaling response (P. E. Hughes, et al., *J. Biol. Chem.* 270:12411–12417, (1995); J. Ylanne, et al., *J. Biol. Chem.* 270:9550–9557, (1995)).

Chimeric, transmembrane proteins containing the cytoplasmic domain of GP IIIa, but not of GP IIb, inhibit the function of GP IIb–IIIa (Y. P. Chen et al., *J. Cell Biol.* 269:18307–18310, (1994)), implying that free GP IIIa cytoplasmic domains bind proteins within cells which are necessary for normal GP IIb–IIIa function. Several proteins have been shown to bind either the transmembrane domains or the cytoplasmic domains of GP IIb or GP IIIa.

CD-9, a member of the tetraspanin family of proteins (F. Lanza, et al., *J. Biol. Chem.* 266:10638–10645, 1991), has been found to interact with GP IIb–IIIa on aggregated platelets. β3-endonexin, a protein identified through two hybrid screening using the cytoplasmic domain of GP IIIa as the "bait", has been found to interact directly and selectively with the cytoplasmic tail of GP IIIa (S. Shattil et al., *J. Cell. Biol.* 131:807–816, (1995)). β3-endonexin shows decreased binding to the GP IIIa cytoplasmic domain containing the thrombasthenic S752-P mutation. It is not yet known whether either of these GP IIIa-binding proteins are involved in signal transduction.

Cytoplasmic proteins that bind to αVβ3 have also been described which may be interacting with the integrin at the GP IIIa cytoplasmic domain sequence. Bartfeld and coworkers (N. S. Bartfeld et al., *J. Biol. Chem.* 268:17270–17276, (1993)) used immunoprecipitation from detergent lysates to show that a MW=190-kDa protein associates with the αVβ3 integrin from PDGF-stimulated 3T3 cells. IRS-1 was found to bind to the αVβ3 integrin following insulin stimulation of Rat-1 cells stably transfected with DNA encoding the human insulin receptor (K. Vuori and E. Ruoslahti, *Sci.* 266:1576–1578, (1994)). Kolanus et al. (*Cell* 86:233–242, (1996)) recently identified Cytohesin-1. Cytohesin-1 specifically binds to the intracellular portion of the integrin β2 chain, and overexpression of cytohesin-1 induces β2 integrin-dependent binding of Jurkat cells to ICAM-1. A novel serine/threonine kinase, ILK-1, was found to associate with the β1 cytoplasmic domain (Hannigan et al., *Nature* 379: 91–96, (1996)). Overexpression of ILK-1 inhibits adhesion to the integrin ligands fibronectin, laminin, and vitronectin.

Integrin binding to adhesive proteins and integrin signal transduction have a wide variety of physiological roles, as identified above. Enhanced signaling through integrins allows for increased cell adhesion and activation of intracellular signaling molecules which causes enhanced cell mobility and growth, enhanced cell responsiveness, and modulations in morphological transformations. Although integrins responsible for cellular function have been described and signaling events are beginning to be elucidated, the mechanism by which integrins transduce signals remains to be determined. To understand the molecular mechanisms of the inside-out and outside-in signaling roles mediated by the cytoplasmic tails of β3 integrin requires the identification of the intracellular molecules that interact with the intracellular tails of integrin. It has been reported that α-actinin binds to β1 tails in vitro (Otey et al. *J. Biol. Chem.* 268:21193–21197, (1993)) but the functional relevance of these bindings is not clear. By using yeast two-hybrid, ILK-1 was identified as a β1 interacting protein but ILK-1 does not bind to β3 (Hannigan et al., *Nature* 379:91–96 (1996)).

F. Homologous Recombination

Genes can be introduced in a site directed fashion using homologous recombination. This can be used in the creation of a transgenic animal, wherein the animal would be mutated, and the phenotype of the mutation could be studied for purposes of drug screening, investigating physiologic processes, developing new products and the like. Papers discussing homologous recombination are discussed in R. Kucherlapati et al., (1995) U.S. Pat. No. 5,413,923.

Homologous recombination permits site-specific modifications in endogenous genes and thus inherited or acquired mutations may be corrected, and/or novel alterations may be engineered into the genome. The application of homologous recombination to gene therapy depends on the ability to carry out homologous recombination or gene targeting in normal, somatic cells for transplantation.

To prepare cells for homologous recombination, embryonic stem cells or a stem cell line may be obtained. Cells other than embryonic stem cells can be utilized (e.g. hematopoietic stem cells etc.) (See for more examples, J. G. Seidman et al., (1994) U.S. Pat. No. 5,589,369). The cells may be grown on an appropriate fibroblast fetal layer or grown in the presence of leukemia inhibiting factor (LIF) and then used. The embryonic stem cells may be injected into a blastocyst, that has been previously obtained, to provide a chimeric animal. The main advantage of the embryonic stem cell technique is that the cells transfected with the "transgene" can be tested prior to reimplantation into a female animal for gestation for integration and the effect of the transgenes. In contrast to the conventional microinjection technique, the homologous respective endogenous gene can be removed from a chromosome by homologous recombination with the transgene. By subsequent cross-breeding experiments, animals can be bred which carry the transgene on both chromosomes. If mutations are incorporated into the transgenes which block expression of the normal gene production, the endogenous genes can be eliminated by this technique and functional studies can thus be performed.

Homologous recombination can also proceed extrachromasomally, which may be of benefit when handling large gene sequences (e.g., larger than 50 kb). Methods of performing extrachromosomal homologous recombination are described in R. M Kay et al., (1998) U.S. Pat. No. 5,721,367.

G. Production of Transgenic Animals

Transgenic animals are genetically modified animals into which cloned genetic material has been experimentally transferred. The cloned genetic material is often referred to as a transgene. The nucleic acid sequence of the transgene is integrated at a locus of a genome where that particular nucleic acid sequence is not otherwise normally found. The transgene may consist of nucleic acid sequences derived from the genome of the same species or of a different species than the species of the target animal.

The development of transgenic technology allows investigators to create mammals of virtually any genotype and to assess the consequences of introducing specific foreign nucleic acid sequences on the physiological and morphological characteristics of the transformed animals. The availability of transgenic animals permits cellular processes to be influenced and examined in a systematic and specific manner not achievable with most other test systems. For example, the development of transgenic animals provides biological and medical scientists with models that are useful in the study of disease. Such animals are also useful for the testing and development of new pharmaceutically active substances.

Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al., *Hypertension* 22(4):630–633 (1993); Brenin et al., *Surg. Oncol.* 6(2)99–110 (1997); Tuan (ed.), *Recombinant Gene Expression Protocols*, Methods in Molecular Biology No. 62, Humana Press (1997)). The term "knock-out" generally refers to mutant organisms, usually mice, which contain a null allele of a specific gene. The term "knock-in" generally refers to mutant organisms, also usually mice, into which a gene has been inserted through homologous recombination. The knock-in gene may be a mutant form of a gene which replaces the endogenous, wild-type gene.

A number of recombinant murines have been produced, including those which express an activated oncogene sequence (U.S. Pat. No. 4,736,866); express simian SV 40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess an bovine growth hormone gene (Clutter et al., *Genetics* 143(4):1753–1760 (1996)); and, are capable of generating a fully human antibody response (McCarthy, *The Lancet* 349(9049):405 (1997)).

While murines, especially mice and rats, remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al., *Mol. Reprod. Dev.* 46(4(:515–526 (1997); Houdebine, *Reprod. Nutr. Dev.* 35(6):609–617 (1995); Petters, *Reprod. Fertil. Dev.* 6(5):643–645 (1994); Schnieke et al., *Science* 278(5346):2130–2133 (1997); and, Amoah, *J. Animal Science* 75(2):578–585 (1997)).

The method of introduction of nucleic acid fragments into recombination competent mammalian cells can be by any method which favors co-transformation of multiple nucleic acid molecules. Detailed procedures for producing transgenic animals are readily available to one skilled in the art, including the recitations in U.S. Pat. No. 5,489,743 and U.S. Pat. No. 5,602,307.

SUMMARY OF THE INVENTION

The present invention provides non-human mammals comprising altered, substituted or mutant integrin cytoplasmic β subunit genes (and their expression products) in which at least one of the two (or more) cytoplasmic tyrosine residues of the expression product are replaced with a non-tyrosine residue such as phenylalanine. Examples of mammals encompassed by the present invention include sheep, goat, mouse, pig, dog, cat, monkey, chimpanzee, hamster, rat, rabbit, cow and guinea pig.

More specifically, the present invention provides non-human mammals comprising a mutant GP IIIa gene and expression product wherein one or both of the cytoplasmic tyrosine residues that are capable of phosphorylation have been replaced with a non-phosphorylatable residue such as phenylalanine.

Even more specifically, the present invention provides transgenic mice comprising a mutant GP IIIa gene wherein the two cytoplasmic tyrosine residues 747 and 759 have each been replaced with phenylalanine.

The present invention also provides platelets isolated from the blood plasma of the transgenic non-human mammals of the present invention.

The present invention also provides methods of preparing a transformed non-human mammal with a mutant integrin cytoplasmic β subunit gene, such as the GP IIIa gene, wherein, for example, at least one of the two tyrosine residues of the endogenous GP ma gene has been replaced with a non-tyrosine residue to prepare the mutant GP IIIa, wherein the methods comprise: a) introducing into embryonic stem cells a nucleic acid molecule encoding the mutant integrin cytoplasmic β subunit gene, such as a mutant or altered GP IIIa gene, and b) regenerating a transformed non-human mammal from the cells resulting from step a).

More specifically, the present invention provides methods of preparing a transformed non-human mammal with, for example, a mutant GP IIIa gene wherein at least one of the two tyrosine residues of the endogenous GP IIIa gene has been replaced with a non-tyrosine residue to prepare the mutant GP IIIa, said method comprising:
  a) introducing into embryonic stem cells a nucleic acid molecule encoding the mutant GP IIIa gene and a selectable marker flanked by FRT sites;
  b) identifying and selecting transformed cells;
  c) removing the selectable marker from the transformed cells selected in step b) by transient transformation with FLP recombinase;
  d) injecting the transformed cells from step c) into blastocysts;
  e) regenerating a transformed non-human mammal from the blastocysts of step d), wherein the regenerated transformed non-human mammal is chimeric for the mutant GP IIIa gene;
  f) breeding the chimeric non-human mammal with a wild-type non-human mammal to produce a non-human mammal heterozygotic for the mutant GP ma gene;
  g) crossing a heterozygotic non-human mammal produced in step f) with a second heterozygotic non-human mammal produced in step f); and,
  h) selecting a non-human mammal homozygotic for the mutant GP IIIa gene from the resulting progeny.

The present invention also provides methods of comparing a characteristic between two mammals of the same species, or strain, wherein one mammal has, for example, a wild-type GP IIIa gene and the other mammal has an altered or mutant GP IIIa gene, wherein at least one of the two tyrosine residues of the wild-type GP IIIa gene has been replaced with a non-tyrosine residue in the mutant GP IIIa gene. More specifically, the present invention includes such methods using transgenic mammals wherein both cytoplasmic tyrosine residues of GP IIIa have been replaced with a non-tyrosine residue such as phenylalanine. Even more specifically, the present invention includes such methods using transgenic mammals wherein the cytoplasmic tyrosine residues 747 and 759 have both been replaced with a non-tyrosine residue such as phenylalanine.

Examples of characteristics which can be compared use in the transgenic mammals of the present invention include comparing various physiological or biological functions and responses that are mediated, in whole or in part, by the cytoplasmic β subunit gene of various integrin molecules. For example, a comparison of such functions would include observations and comparisons of the bleeding or clotting time between the two mammal types (i.e., between wild-type and genetically engineered animals); comparing various thrombotic responses between the two mammal types; comparing the level, extent and rate of angiogenesis between the two mammal types in response to various angiogenic stimulii; comparing the rate and extent of tumor metastasis between the two mammal types; and comparing scope, rate and extent of inflammation between the two mammal types.

The present invention also provides methods of determining the effect of various agents on selected biological characteristics of a genetically engineered mammal expressing an altered or mutant integrin β subunit gene that is attributable to the expression of the GP IIIa gene, wherein the methods comprise: a) administering said agent to the transgenic mammal; b) maintaining said mammal for a desired period of time after said administration; and, c) determining whether a characteristic of said mammal that is attributable to the expression of the mutant GP IIIa gene has been affected by the administration of said agent.

Further objects and advantages of the present invention will be clear from the description and examples which follow. For example, even though the examples are directed to transgenic animals comprising mutant β3 subunits, the present invention can be practiced with other integrin β subunits that have one or more phosphorylatable tyrosine residues in the endogenous gene coding for that particular integrin β subunit gene.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

I. General Description

The following discussion presents a general description of the invention as well as definitions for certain terms used herein. Portions of the invention described in this application were described by David R. Phillips at the American Heart Association meeting in San Francisco, Calif. on Apr. 15, 1998. The content of that presentation and any printed material related thereto are herein incorporated by reference in their entirety.

Previous work by the present inventors indicated that the tyrosine phosphorylation of the GP IIIa subunit of the platelet integrin GP IIb–IIIa (also known as αIIbβ3) could modulate signal transduction by this integrin (see, e.g., U.S. patent application Ser. No. 08/975,653, filed Nov. 21, 1997, which is incorporated by reference herein). That GP IIIa tyrosine phosphorylation was dependent upon platelet aggregation, and the fact that signaling proteins as well as cytoskeletal proteins became associated with the phosphorylated GP IIIa, suggested to us that GP IIIa phosphorylation was important in outside-in GP IIb–IIIa signaling in platelets. Successful GP IIb–IIIa-mediated outside-in signaling is required for platelet functions such as the formation of stable platelet aggregates, an important process for normal hemostasis and one which, under aberrant conditions, can lead to the formation of occlusive thrombi. Thus, if tyrosine phosphorylation of GP IIIa is indeed a critical step in outside-in GP IIb–IIIa signaling, then it could be hypothesized that compounds capable of inhibiting such a phosphorylation event would have anti-thrombotic properties. To address the importance of tyrosine phosphorylation of GP IIIa in platelet function a mutant mouse has been generated in which the endogenous GP IIIa gene was replaced with one in which the two cytoplasmic tyrosine residues were mutated to phenylalanines (GP IIIa (Y747F, Y759F)). The platelets from such animals express GP IIIa that can not undergo tyrosine phosphorylation and therefore provide a critical tool for assessing the importance of the phosphorylation reaction for platelet function.

Although assessing the effect of GP IIIa mutations in transfected cell lines (i.e., in vitro) is useful in determining the role of various residues in GP IIIa function, the importance of the GP IIIa cytoplasmic tyrosine residues in platelet function can best be determined in vivo. Thus we undertook a gene replacement project in which the endogenous murine GP IIIa gene was replaced by a mutant genes with at least one non-tyrosine substitution at one of the two cytoplasmic tyrosine residues. More specifically, the endogenous murine GP IIIa gene was replaced by a mutant gene with double tyrosine to phenylalanine substitutions in the cytoplasmic domain at positions 747 and 759 respectively. Since the murine GP IIIa gene has not been sequenced, P1 clones containing murine genomic GP IIIa were obtained using PCR-based technology with PCR primers based on the sequence of the human GP IIIa gene. DNA corresponding to the area of interest, i.e. the two exons encoding the GP ma cytoplasmic domain, was mapped using common molecular biology techniques. The two tyrosines in the cytoplasmic domain (Y747 and Y759) were mutated to phenylalanines and a targeting vector was constructed which included the mutated GP IIIa genomic DNA as well as a selectable drug marker (neomycin resistance) flanked by FRT sites, the recognition sequences for the FLP recombinase. This vector was transfected into embryonic stem cells and cells which had undergone a homologous recombination event were identified by Southern blotting and by PCR using specific primers. Those ES cells that contained one normal GP IIIa allele and one GP IIIa (Y747F, Y759F) mutant allele as well as the neomycin resistance DNA were then transiently transfected with the FLP recombinase to remove the drug resistance DNA. Again, ES cells that had undergone the desired event were identified by both Southern blotting and PCR. The now standard protocols for the generation of mutant mice were employed. Basically, the desired mutant ES cells being injected into blastocysts in order to generate chimeric mice which were bred to wild-type mice to produce heterozygote animals expressing one normal and one mutant GP IIIa allele (as assessed by Southern blotting of tail genomic DNA and PCR). These heterozygote animals were then crossed to generate litters in which ~¼ of the animals were homozygote for mutant GP IIIa (ie. the only GP IIIa expressed by these mice contained the double tyrosine to phenylalanine mutation).

These transgenic mice provide a critical tool for assessing the importance of the GP IIIa cytoplasmic tyrosine residues on platelet function. Previous work indicated that phosphorylation of the GP IIIa tyrosine residues was important in outside-in GP IIb–IIIa signaling. The platelets from the mutant mice express a GP IIb–IIIa in which the GP IIIa can not be tyrosine phosphorylated. Thus platelets from these mice can be used in a number of assays to assess the role of outside-in GP IIb–IIIa signaling on platelet function. For example, bleeding time in mutant mice will assess whether tyrosine phosphorylation of GP IIIa is critical for normal hemostasis. Also if GP IIIa tyrosine phosphorylation is an obligatory part of outside-in signaling, one would predict that mutant mice to be defective in thrombotic responses, where the formation of very large platelet aggregates is required. We can now employ murine thrombotic models with these mutant mice to directly assess this issue. Indeed, this mutant mouse will provide information on the utility of generating therapeutics designed to interfere either directly with GP IIIa tyrosine phosphorylation, or with an event dependent on this phosphorylation e.g. interaction of phospho-GP IIIa with an adaptor protein.

Expression of the GP IIIa ($\beta_3$) integrin subunit is not restricted to platelets. In endothelial cells this protein pairs with the $\alpha_v$ subunit to form the $\alpha_v\beta_3$ integrin. This integrin appears to play an important role in angiogenesis and tumor metastasis. In neutrophils, $\beta_3$ is a subunit of the LRI (leucocyte responsive integrin), and is thought to be involved in inflammatory responses. Since all of the $\beta_3$ in the mutant mouse contains the tyrosine to phenylalanine mutations in the cytoplasmic domain, this mouse can be used to examine the effect of these mutations on $\alpha_v\beta_3$ and LRI function. Again, such analyses will provide information on whether or not inhibition of $\beta_3$ phosphorylation will have effects on angiogenesis, tumor metastasis and/or inflammation, and thus will be of significant clinical import.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

II. Specific Embodiments

Figure 2:
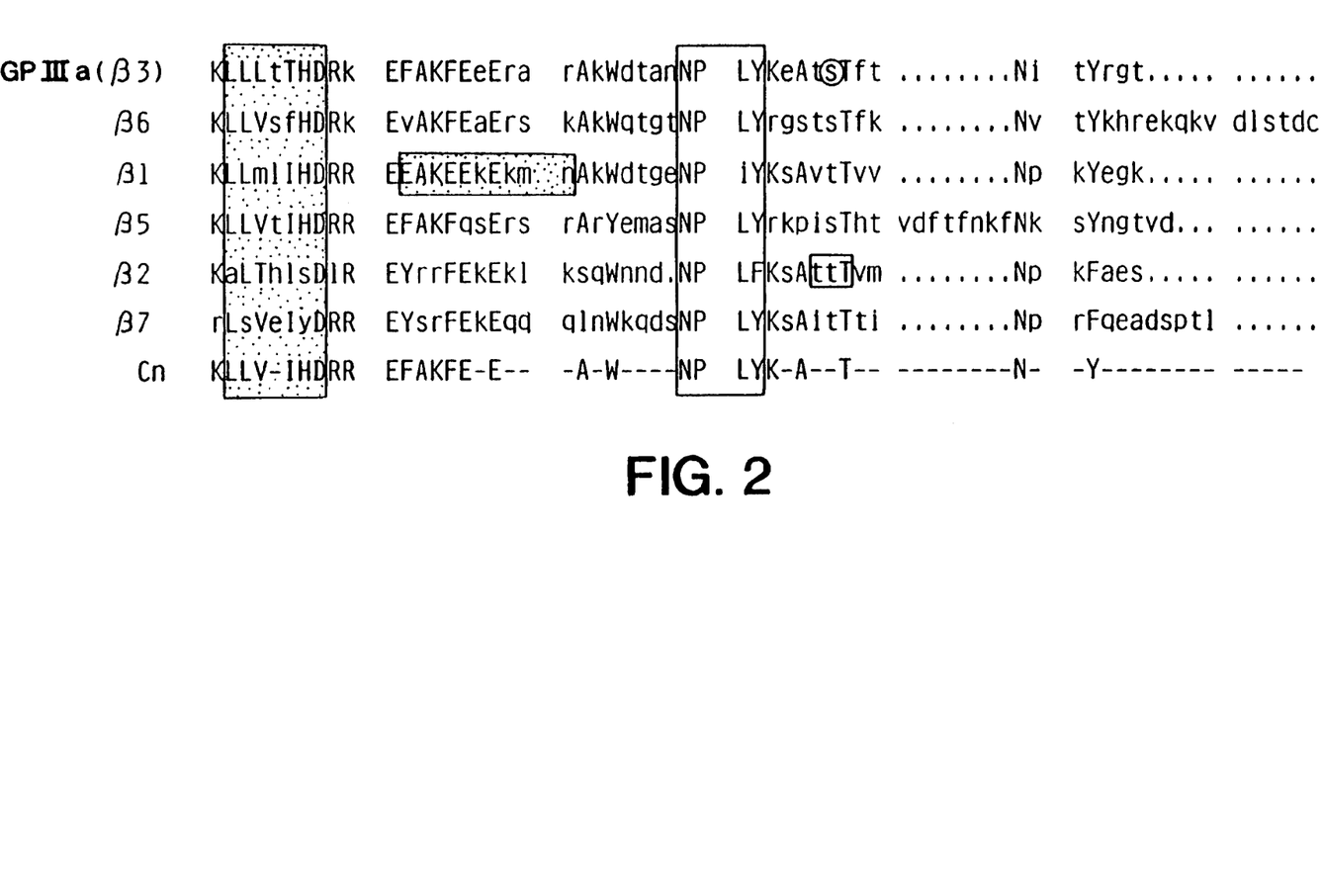
FIG. 2 shows the cytoplasmic domain of various integrin subunits: GP IIIa (β3), SEQ ID NO:1; β6, SEQ ID NO:2; β1, SEQ ID NO:3; β5, SEQ ID NO:4; β2, SEQ ID NO:5; β7, SEQ ID NO:6; and a consensus sequence for the cytoplasmic domain of β integrin subunits, SEQ ID NO:7.

The presence of phosphotyrosine binding motifs within the cytoplasmic domain of $\beta 3$ suggests that tyrosine phosphorylation of this integrin tail facilitates the recruitment of phosphotyrosine-binding signaling proteins Shc and Grb2 to the cell membrane. See Philips et al. (1996). The present inventors have discovered that tyrosine phosphorylation and dephosphorylation of the $\beta 3$ integrin tail may, in an analogous manner, regulate integrin association with the cytoskeleton (see, e.g., U.S. patent application Ser. No. 08/975, 653, filed Nov. 21, 1997, which is incorporated by reference herein). FIG. 2 provides the amino acid sequences of various human integrin $\beta$ subunits, showing the locations of the tyrosine residues. As mentioned previously, other studies have shown that the sequences of the cytoplasmic domains of $\beta 1$, $\beta 2$ and $\beta 3$ (GP IIIa) which contain tyrosines are important for normal functioning of GPIIb–IIIa and of other integrins. Thus, transgenic animals that express altered and mutant cytoplasmic domains of those or other integrin $\beta$ subunits that natively contain phosphorylatable tyrosine residues are expressly included in the scope of this invention.

Also expressly contemplated are altered, modified or mutated integrin subunits that contain conservative substitutions for the phosphorylatable tyrosine residues. As used herein, a conservative amino acid substitution refers to alterations of particular residues (specifically the phosphorylatable tyrosine residues) or other alterations in the amino acid sequence that, except for the inability to undergo phosphorylation at the site of the one or more relevant cytoplasmic tyrosine residues, do not otherwise adversely affect the ability of the integrin to participate in signaling activities or to bind to one or more particular binding partners, such as myosin, for example. A substitution, insertion or deletion is said to adversely affect the normal functioning of the corresponding wild-type integrin $\beta$ subunit peptide when the altered sequence significantly inhibits the peptide from participating in signalling activities or from associating with its native binding partners, such as myosin. For example, it is contemplated that the overall charge, structure or hydrophobic/hydrophilic properties of the $\beta$ subunit peptide can be altered without adversely affecting activity of the peptide. Accordingly, it is contemplated that the amino acid sequence of the $\beta$ subunit peptide can be altered, for example to render the peptide more hydrophobic or hydrophilic, to the extent that this does not adversely affecting the ability of the peptide to otherwise participate in its normal signalling activities or to become associated with normal binding partners, such as myosin. Thus, specifically contemplated are mutant GPIIIa subunits which are For example, in one application, altered $\beta$ subunit peptides can be generated using standard knock-out procedures to modify any one or all of the phosphorylatable tyrosine residues. This can be accomplished using a variety of art-known procedures such as targeted recombination. Once generated, the genetically-engineered animal can be used to 1) identify biological and pathological processes mediated by the $\beta$ subunit peptide; 2) identify proteins and other genes that interact with the $\beta$ subunit peptide; 3) identify agents that can be exogenously supplied to overcome the absence or reduction in phosphorylation of the $\beta$ subunit peptide; and 4) serve as an appropriate screen for identifying agents that modulate (i.e., increase or decrease) the activity of the altered $\beta$ subunit peptides.

As discussed herein, the present invention provides transgenic animals that contain non-tyrosine residues at sites where phosphorylatable tyrosine residues occur normally in endogenous $\beta$ subunit genes. Since the non-tyrosine substitutions will not be phosphorylated as in the case where the residues are tyrosine and since normal platelet aggregation is dependent on phosphorylation occurring, the transgenic mammals of the present invention will display non-normal platelet aggregation. By comparing the physiological and morphological characteristics between the transformed and non-transformed animals one skilled in the art can thereby determine the effect of the presence or absence of cytoplasmic tyrosine phosphorylation in the GP IIIa gene on the corresponding animal.

Furthermore, the transgenic animals of the present invention can be used to identify agents that modulate (i.e., either promote or further inhibit) platelet aggregation or other effects that are mediated by integrin signaling pathways. The evaluation of such agents can be conducted either in vitro, in situ, or in vivo by techniques known to those skilled in the art. The cells, platelets, tissues and whole organisms of the disclosed transgenic animals have utility in testing the effect of various agents for their ability to reduce or increase the processes involved with integrin-mediated cytoskeletal association. Agents which can be tested include various anticoagulant, thrombolytic and antiplatelet therapeutics and drugs. Examples of such agents include glycosaminoglycans such as heparin; oral anticoagulants such as dicumarol, anisindione, and bromadkiolone; tissue plasminogen activator (t-PA); urokinase; aspirin; dipyridamole; and ticlopidine. See, Majerus, et al., *Anticoagulant, Thrombolytic, and Antiplatelet Drugs*, in Goodman & Gilman's The Pharmacological Basis of Therapeutics, Ninth Edition, Chapter 54 (1996) for a more complete list of such agents and their pharmacology.

The cells and whole organisms of the transgenic animals of the present invention, quite apart from their uses in veterinary and human medicine, may also be used to investigate gene regulation, expression and organization in animals. By studying the various effects of altered or mutant integrin β subunits, for example the GP IIIa gene, on other cells, tissues and biological processes, one skilled in the art can ascertain the role of tyrosine phosphorylation in the normal metabolic pathways.

For further examples of diagnostic and research uses of transgenic mammals, especially transgenic mice, see U.S. Pat. No. 5,569,824.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

was close in size to the predicted human fragment (~1.2 kB) which spanned the 3' part of exon M, the 5' part of exon N, and the intron between these two exons. The primers encoded: 1) 5' primer—residues 1834–1850 and 2) 3' primer—residues 2026–2039 of murine GP IIIa. These specific primers were then used to obtain a P1 clone containing a large fragment of murine genomic DNA which gave the same band when used as a template in PCR. Thus, we had obtained a P1 clone that contained murine genomic GP IIIa, and specifically contained the regions encoding the cytoplasmic domain of GP IIIa. Next, ~10 kB of this P1 clone was mapped by a mixture of restriction digests, Southern Blotting and amino acid sequencing. It was confirmed that this was murine GP IIIa and that, similar to human GP IIIa, two exons (termed M and N after the human nomenclature) encoded the murine GP IIIa cytoplasmic region. Indeed the cytoplasmic domain amino acid residues turned out to be identical between human and mouse.

The amino acid sequence having SEQ ID NO. 1 is as follows:

```
GPNICTTRGV SSCQQCLAVS PMCAWCSDEA LPLGSPRCDL KENLLKDNCA PESIEFPVSE   60

ARVLEDRPLS DKGSGDSSQV TQVSPQRIAL RLRPDDSKNF SIQVRQVEDY PVDIYYLMDL  120

SYSMKDDLWS IQNLGTKLAT QMRKLTSNLR IGFGAFVDKP VSPYMYISPP EALENPCYDM  180

KTTCLPMFGY KHVLTLTDQV TRFNEEVKKQ SVSRNRDAPE GGFDAINQAT VCDEKIGWRN  240

DASHLLVFTT DAKTHIALDG RLAGIVQPND GQCHVGSDNH YSASTTMDYP SLGLMTEKLS  300

QKNINLIFAV TENVVNLYQN YSELIPGTTN GVLSMDSSNV LQLIVDAYGK IRSKVELEVR  360

DLPEELSLSF NATCLNNEVI PGLKSCMGLK IGDTVSFSIE AKVRGCPQEK EKSFTIKPVG  420

FKDSLIVQVT FDCDCACQAQ AEPNSHRCNN GNGTFECGVC RCGPGWLGSQ CECSEEDYRP  480

SQQDECSPRE GQPVCSQRGE CLCGQCVCHS SDFGKITGKY CECDDFSCVR YKGEMCSGHG  540

QCSCGDCLCD SDWTGYYCNC TTRTDTCMSS NGLLCSGRGK CECGSCVCIQ PGSYGDTCEK  600

CPTCPDACTF KKECVECKKF DRGALHDENT CNRYCRDEIE SVKELKDTGK DAVNCTYKNE  660

DDCVVRFQYY EDSSGKSILY VVEEPECPKG PDILVVLLSV MGAILLIGLA ALLIWKLLIT  720

IHDRKEPAKF EEERARAKWD TANNPLYKEA TSTFTNITYR GT                    762
```

Other generic configurations will be apparent to one skilled in the art.

EXAMPLE 1

Obtaining Murine Genomic GP IIIa DNA

The sequence for the murine genomic DNA is not known and has not been published, however part of the amino acid sequence of mouse GP IIIa was available (Cietat et al. (1993) *Biochem et Biophys Res Comm.* 193: 771–778, and Dr Jean-Phillipe Rosa, Unite INSERM 348, Paris) and its similarity to human GP IIIa sequence suggested the genomic GP IIIa from humans and mice could be fairly similar. Therefore, several PCR primers were generated towards the mouse GP IIIa sequence in areas which, in the case of human GP IIIa (SEQ ID NO. 1), spanned the two exons known to encode the cytoplasmic domain of GP IIIa ie. exons M and N (Lanza, F. et al. (1990) *J. Biol. Chem.* 265: 18098–18103). These primers were then tested with total murine genomic DNA and one set generated a specific band of approximately 1.5 kB in the PCR (polymerase chain reaction). This band

EXAMPLE 2

Mutation of Tyrosine Residues 747 and 759 to Phenylalanines

A 0.3 kB PstI/SacI fragment containing exon N (which encodes the two tyrosine residues) was subcloned into pBSKS II and the two tyrosine residues were mutated to phenylalanines using standard site-directed mutagenesis techniques. Mutations were confirmed by sequencing and were also designed to introduce two new enzyme sites, a DraI site (at Y747F) and a TaqI site (at Y759F) which could be used in later identification of the mutant DNA. This mutant fragment was used to replace the wild-type PstI/SacI fragment in the murine genomic GP IIIa clone.

EXAMPLE 3

Construction of Targeting Vector

An approximately 2.5 kB EcoRI/HindIII fragment of murine GP IIIa, containing exon M as well as intronic genomic DNA was subcloned, using HindIII/EcoRI adaptors, into an EcoRI site of a pBS vector containing a neomycin resistant cassette. The neo$^r$ DNA was flanked by FRT recognition sequences which are sites recognized by the Flp recombinase that can be used to excise the neo$^r$ DNA at a later stage (Dymecki S. M. (1996) *PNAS USA* 93: 6191–6196). A ~4 kB HindIII fragment of GP IIIa containing exon N with the tyrosine to phenylalanine mutations was subcloned into a HindIII site on this vector to give a construct basically consisting of the mutated GP IIIa with a neo$^r$ cassette in the intron between exons M and N.

EXAMPLE 4

Generation of Targeted Embryonic Stem (ES) Cells

The above targeting construct was transfected into ES cells which were then selected for neo$^r$ using the drug G418 as described in Johnson, R and Killeen, N. P (In Gene Probes 2: a practical approach, Eds. B. D. Hanes and S. J. Higgins. Oxford University Press p. 313–327 (1995)). ES cell which had undergone a successful homologous recombination event were identified by Southern blotting and PCR techniques. These cells now had one wild type GP ma allele and one containing the neo$^r$ cassette and the tyrosine to phenylalanine mutations. The drug cassette is 1.9 kB in size and although it was present in an intron we wished to remove it to make sure that its presence would have no detrimental effect in our experiments. To this effect the selected ES cells were transiently transfected with the Flp recombinase which recognized the FRT sites and led to the excision of the DNA encoding the drug resistance. Thus, instead of a 1.9 kB piece of extraneous DNA being present in the intron a small piece encoding the 34 bp FRT recognition site (and a new XbaI site) is all that remains (Dymecki, S. M., *PNAS* 93: 6191–6196 (1996)). Again, ES cells that had undergone a successful event were selected for using Southern blotting and PCR techniques.

EXAMPLE 5

Generation of Mutant Mice

To produce mutant mice a mutant ES cell clone (originally from a strain 129 mouse) was injected into blastocysts from a C57B16 mouse and these blastocysts were implanted into a pseudo-pregnant foster mother (as in Ramirez-Solis, R., Davis, A. C., and Bradley, A. *Guide to techniques in mouse development*. Methods in Enzymology 225. Eds. P. M. Wassarman, M. L. DePanphilis. Academic Press (1993) in particular p 855–878). Male chimeric animals identified by their mixed coat color (black from the C57B16 blastocyst and agouti from the 129 ES cells) were then mated with C57B16 wild-type females. The offspring were genotyped for the presence of wildtype and mutant GP IIIa alleles by Southern blotting (making use of the new XbaI site that was present only in mutant GP IIIa DNA). The offspring were a mix of wild-type and heterozygote animals and the heterozygote animals were further crossed to produce litters containing wildtype animals, heterozygote animals (ie. one wild-type and one mutant GP IIIa allele) and homozygotes (ie. both GP IIIa alleles containing the tyrosine to phenylalanine mutations).

To date the genotypes of the offspring from such matings have occurred in the expected ratio (assuming basic Mendelian genetics). Furthermore, the mutant animals are viable and express GP IIb–IIIa on their platelets at similar levels to that seen in normal animals expressing non-mutant GP IIIa when the platelets are stained with an anti-GP IIb–IIIa antibody and examined on the FACS (fluorescent activated cell sorter).

Although the present invention has been described in detail with reference to examples above, it is understood that various modifications can be made without departing from the spirit of the invention. Accordingly, the invention is limited only by the following claims. All cited patents, applications and publications referred to in the application are hereby incorporated by reference in their entirety.

What is claimed is:

1. A transgenic mouse which expresses a transgene integrated into its genome, wherein the transgene comprises DNA encoding a mutant GP IIIa ($\beta_3$) protein having two conservative amino acid substitutions for two wild type tyrosine residues in its mutant cytoplasmic domain, wherein said transgenic mouse has platelets with reduced or absent phosphorylation of said mutant GP IIIa ($\beta_3$) protein compared to platelets with wild type GP IIIa ($\beta_3$) protein from a wild type mouse.

2. The transgenic mouse of claim 1 wherein the mutant cytoplasmic domain comprises conservative amino acid substitutions for the wild type tyrosine residues depicted in the cytoplasmic domain sequence for GP IIIa in FIG. 2 (SEQ ID NO: 1).

3. The transgenic mouse of claim 1 wherein each cytoplasmic wild type tyrosine residue is substituted by a mutant phenylalanine residue.

4. A method of determining the effect of an agent on a biological response of the transgenic mouse of claim 1, wherein the biological response is mediated by GP IIIa ($\beta_3$) phosphorylation, the method comprising:
   a). administering the agent to the mouse;
   b). determining the effect of the agent on the biological response mediated by GP IIIa ($\beta_3$) phosphorylation.

5. The transgenic mouse of claim 1, wherein the DNA encoding the mutant GPIIIa replaces the DNA encoding the wild type GP IIIa.

6. The transgenic mouse of claim 5, wherein replacement of the DNA encoding the wild type GP IIIa results in a transgenic mouse which is heterozygous for the DNA encoding the mutant GP IIIa gene.

7. The transgenic mouse of claim 5, wherein replacement of the DNA encoding the wild type GP IIIa results in a transgenic mouse which is homozygous for the DNA encoding the mutant GP IIIa gene.

8. Platelets isolated from blood plasma of the transgenic mouse of claim 7.

9. A method of determining the effect of an agent on a biological response of the transgenic mouse of claim 7, wherein the biological response is mediated by GP IIIa ($\beta_3$) phosphorylation, the method comprising:
   a). administering the agent to the mouse;
   b). determining the effect of the agent on the biological response mediated by GP IIIa ($\beta_3$) phosphorylation.

10. Platelets isolated from blood plasma of the transgenic mouse of claim 1.

11. A method of preparing a transgenic mouse heterozygous for a mutant GP IIIa ($\beta_3$) gene, wherein the mutant gene encodes a mutant GP IIIa ($\beta_3$) protein having two conservative amino acid substitutions for two wild type tyrosine residues in its mutant cytoplasmic domain, the method comprising:
   a) introducing into embryonic stem cells a nucleic acid molecule comprising the mutant GP IIIa ($\beta_3$) gene, wherein the mutant gene encodes the mutant GP IIIa ($\beta_6$) protein;
   b) injecting transformed cells from step a) into one or more blastocysts; and
   c) generating a chimeric mouse from the blastocysts of step b);
   d) mating the chimeric mouse of step c) with a wild type mouse to obtain a transgenic mouse heterozygous for a mutant GP IIIa ($\beta_3$) gene,
wherein said transgenic mouse has platelets with reduced or absent phosphorylation of said mutant GP IIIa ($\beta_3$) protein compared to platelets with wild type GP IIIa ($\beta_3$) protein from a wild type mouse.

12. The method of claim 11 wherein the mutant cytoplasmic domain comprises a conservative amino acid substitutions for the wild type tyrosine residues depicted in the cytoplasmic domain sequence for GP IIIa in FIG. 2 (SEQ ID NO: 1).

13. The method of claim 11 wherein each conservative amino acid substitute in the mutant cytoplasmic domain is phenylalanine.

14. The method of claim 11 further comprising:
   e) mating the transgenic mouse; and
   f) selecting a mouse homozygous for the mutant GP IIIa ($\beta_3$) gene.

15. A method of preparing a transgenic mouse heterozygous for a mutant GP IIIa ($\beta_3$) gene encoding a mutant GP IIIa ($\beta_3$) protein having two conservative amino acid substitutions for two wild type tyrosine residues in its mutant cytoplasmic domain, the method comprising:
   a) introducing into embryonic stem cells a nucleic acid molecule comprising the mutant GP IIIa ($\beta_3$) gene encoding the mutant GP IIIa ($\beta_3$) protein and a selectable marker flanked by FRT sites, to produce one or more transformed embryonic stem cells;
   b) identifying and selecting the transformed cells;
   c) removing the selectable marker from the transformed cells selected in step b) by transient transformation with FLP recombinase;
   d) injecting transformed cells from step c) into one or more blastocysts; and
   e) generating a transgenic mouse from the blastocysts of step d), wherein the transgenic mouse comprising the mutant GP IIIa gene is heterozygous for the mutant GP IIIa gene,
wherein said transgenic mouse has platelets with reduced or absent phosphorylation of said mutant GP IIIa ($\beta_3$) protein compared to platelets with wild type GP IIIa ($\beta_3$) protein from a wild type mouse.

16. The method of claim 15 wherein each conservative amino acid substitute in the mutant cytoplasmic domain is phenylalanine.

17. The method of claim 15 wherein the mutant cytoplasmic domain comprises conservative amino acid substitutions for the wild type tyrosine residues depicted in the cytoplasmic domain sequence for GP IIIa in FIG. 2 (SEQ ID NO:1).

18. The method of claim 15 further comprising:
   f) mating the transgenic mouse; and
   g) selecting a transgenic mouse homozygous for the mutant GP IIIa ($\beta_3$) gene.

* * * * *

SEQUENCE LISTING

```
<160> NUMBER OF SEQ ID NOS: 7

<210> SEQ ID NO 1
<211> LENGTH: 66
<212> TYPE: PRT
<213> ORGANISM: Mus musculus
<220> FEATURE:
<223> OTHER INFORMATION: Segment of GP IIIa integrin beta-3 subunit
<220> FEATURE:
<221> NAME/KEY: Variant
<222> LOCATION: (1)...(66)
<223> OTHER INFORMATION: Xaa = any amino acid
<220> FEATURE:
<221> NAME/KEY: Variant
<222> LOCATION: (41)...(48)
<223> OTHER INFORMATION: This segment of any amino acids can be from
      zero to eight amino acids long.
<220> FEATURE:
<221> NAME/KEY: Variant
<222> LOCATION: (56)...(66)
<223> OTHER INFORMATION: This segment of any amino acids can be from
      zero to eleven amino acids long.

<400> SEQUENCE: 1

Lys Leu Leu Leu Thr Thr His Asp Arg Lys Glu Phe Ala Lys Phe Glu
  1               5                  10                  15
```

```
Glu Glu Arg Ala Arg Ala Lys Trp Asp Thr Ala Asn Asn Pro Leu Tyr
            20                  25                  30

Lys Glu Ala Thr Ser Thr Phe Thr Xaa Xaa Xaa Xaa Xaa Xaa Xaa
        35                  40                  45

Asn Ile Thr Tyr Arg Gly Thr Xaa Xaa Xaa Xaa Xaa Xaa Xaa
    50                  55                  60

Xaa Xaa
 65

<210> SEQ ID NO 2
<211> LENGTH: 66
<212> TYPE: PRT
<213> ORGANISM: Mus musculus
<220> FEATURE:
<223> OTHER INFORMATION: Segment of integrin beta-6 subunit
<220> FEATURE:
<221> NAME/KEY: Variant
<222> LOCATION: (1)...(66)
<223> OTHER INFORMATION: Xaa = any amino acid
<220> FEATURE:
<221> NAME/KEY: Variant
<222> LOCATION: (41)...(48)
<223> OTHER INFORMATION: This segment of any amino acids can be from
      zero to eight amino acids long.

<400> SEQUENCE: 2

Lys Leu Leu Val Ser Phe His Asp Arg Lys Glu Val Ala Lys Phe Glu
 1               5                  10                  15

Ala Glu Arg Ser Lys Ala Lys Trp Gln Thr Gly Thr Asn Pro Leu Tyr
            20                  25                  30

Arg Gly Ser Thr Ser Thr Phe Lys Xaa Xaa Xaa Xaa Xaa Xaa Xaa Xaa
        35                  40                  45

Asn Val Thr Tyr Lys His Arg Glu Lys Gln Lys Val Asp Leu Ser Thr
    50                  55                  60

Asp Cys
 65

<210> SEQ ID NO 3
<211> LENGTH: 66
<212> TYPE: PRT
<213> ORGANISM: Mus musculus
<220> FEATURE:
<223> OTHER INFORMATION: Segment of integrin beta-1 subunit
<220> FEATURE:
<221> NAME/KEY: Variant
<222> LOCATION: (1)...(66)
<223> OTHER INFORMATION: Xaa = any amino acid
<220> FEATURE:
<221> NAME/KEY: Variant
<222> LOCATION: (41)...(48)
<223> OTHER INFORMATION: This segment of any amino acids can be from
      zero to eight amino acids long.
<220> FEATURE:
<221> NAME/KEY: Variant
<222> LOCATION: (56)...(66)
<223> OTHER INFORMATION: This segment of any amino acids can be from
      zero to eleven amino acids long.

<400> SEQUENCE: 3

Lys Leu Leu Met Leu Ile His Asp Arg Arg Glu Glu Ala Lys Glu Glu
 1               5                  10                  15

Lys Glu Lys Met Asn Ala Lys Trp Asp Thr Gly Glu Asn Pro Ile Tyr
            20                  25                  30

Lys Ser Ala Val Thr Thr Val Val Xaa Xaa Xaa Xaa Xaa Xaa Xaa Xaa
        35                  40                  45
```

```
Asn Pro Lys Tyr Glu Gly Lys Xaa Xaa Xaa Xaa Xaa Xaa Xaa Xaa
         50                  55                  60

Xaa Xaa
 65

<210> SEQ ID NO 4
<211> LENGTH: 66
<212> TYPE: PRT
<213> ORGANISM: Mus musculus
<220> FEATURE:
<223> OTHER INFORMATION: Segment of integrin beta-5 subunit
<220> FEATURE:
<221> NAME/KEY: Variant
<222> LOCATION: (1)...(66)
<223> OTHER INFORMATION: Xaa = any amino acid
<220> FEATURE:
<221> NAME/KEY: Variant
<222> LOCATION: (58)...(66)
<223> OTHER INFORMATION: This segment of any amino acids can be from
      zero to nine amino acids long.

<400> SEQUENCE: 4

Lys Leu Leu Val Thr Ile His Asp Arg Arg Glu Phe Ala Lys Phe Gln
 1               5                  10                  15

Ser Glu Arg Ser Arg Ala Arg Tyr Glu Met Ala Ser Asn Pro Leu Tyr
             20                  25                  30

Arg Lys Pro Ile Ser Thr His Thr Val Asp Phe Thr Phe Asn Lys Phe
         35                  40                  45

Asn Lys Ser Tyr Asn Gly Thr Val Asp Xaa Xaa Xaa Xaa Xaa Xaa
         50                  55                  60

Xaa Xaa
 65

<210> SEQ ID NO 5
<211> LENGTH: 66
<212> TYPE: PRT
<213> ORGANISM: Mus musculus
<220> FEATURE:
<223> OTHER INFORMATION: Segment of integrin beta-2 subunit
<220> FEATURE:
<221> NAME/KEY: Variant
<222> LOCATION: (1)...(66)
<223> OTHER INFORMATION: Xaa = any amino acid
<220> FEATURE:
<221> NAME/KEY: Variant
<222> LOCATION: (41)...(48)
<223> OTHER INFORMATION: This segment of any amino acids can be from
      zero to eight amino acids long.
<220> FEATURE:
<221> NAME/KEY: Variant
<222> LOCATION: (56)...(66)
<223> OTHER INFORMATION: This segment of any amino acids can be from
      zero to eleven amino acids long.

<400> SEQUENCE: 5

Lys Ala Leu Thr His Leu Ser Asp Leu Arg Glu Tyr Arg Arg Phe Glu
 1               5                  10                  15

Lys Glu Lys Leu Lys Ser Gln Trp Asn Asn Asp Xaa Asn Pro Leu Phe
             20                  25                  30

Lys Ser Ala Thr Thr Thr Val Met Xaa Xaa Xaa Xaa Xaa Xaa Xaa
         35                  40                  45

Asn Pro Lys Phe Ala Glu Ser Xaa Xaa Xaa Xaa Xaa Xaa Xaa Xaa
         50                  55                  60

Xaa Xaa
 65
```

```
<210> SEQ ID NO 6
<211> LENGTH: 66
<212> TYPE: PRT
<213> ORGANISM: Mus musculus
<220> FEATURE:
<223> OTHER INFORMATION: Segment of integrin beta-7 subunit
<220> FEATURE:
<221> NAME/KEY: Variant
<222> LOCATION: (1)...(66)
<223> OTHER INFORMATION: Xaa = any amino acid
<220> FEATURE:
<221> NAME/KEY: Variant
<222> LOCATION: (41)...(48)
<223> OTHER INFORMATION: This segment of any amino acids can be from
      zero to eight amino acids long.
<220> FEATURE:
<221> NAME/KEY: Variant
<222> LOCATION: (61)...(66)
<223> OTHER INFORMATION: This segment of any amino acids can be from
      zero to six amino acids long.

<400> SEQUENCE: 6

Arg Leu Ser Val Glu Ile Tyr Asp Arg Arg Glu Tyr Ser Arg Phe Glu
 1               5                  10                  15

Lys Glu Gln Gln Gln Leu Asn Trp Lys Gln Asp Ser Asn Pro Leu Tyr
            20                  25                  30

Lys Ser Ala Ile Thr Thr Thr Ile Xaa Xaa Xaa Xaa Xaa Xaa Xaa Xaa
        35                  40                  45

Asn Pro Arg Phe Gln Glu Ala Asp Ser Pro Thr Leu Xaa Xaa Xaa Xaa
    50                  55                  60

Xaa Xaa
 65

<210> SEQ ID NO 7
<211> LENGTH: 65
<212> TYPE: PRT
<213> ORGANISM: Artificial Sequence
<220> FEATURE:
<223> OTHER INFORMATION: Description of Artificial Sequence: Consensus
      sequence for segment of integrin beta subunits
<220> FEATURE:
<221> NAME/KEY: Variant
<222> LOCATION: (1)...(65)
<223> OTHER INFORMATION: Xaa = any amino acid
<220> FEATURE:
<221> NAME/KEY: Variant
<222> LOCATION: (41)...(48)
<223> OTHER INFORMATION: This segment of any amino acids can be from
      zero to eight amino acids long.
<220> FEATURE:
<221> NAME/KEY: Variant
<222> LOCATION: (56)...(65)
<223> OTHER INFORMATION: This segment of any amino acids can be from
      zero to ten amino acids long.

<400> SEQUENCE: 7

Lys Leu Leu Val Xaa Ile His Asp Arg Arg Glu Phe Ala Lys Phe Glu
 1               5                  10                  15

Xaa Glu Xaa Xaa Xaa Ala Xaa Trp Xaa Xaa Xaa Xaa Asn Pro Leu Tyr
            20                  25                  30

Lys Xaa Ala Xaa Xaa Thr Xaa Xaa Xaa Xaa Xaa Xaa Xaa Xaa Xaa Xaa
        35                  40                  45

Asn Xaa Xaa Tyr Xaa Xaa Xaa Xaa Xaa Xaa Xaa Xaa Xaa Xaa Xaa Xaa
    50                  55                  60

Xaa
 65
```